(12) United States Patent
Zhang et al.

(10) Patent No.: US 10,066,927 B2
(45) Date of Patent: Sep. 4, 2018

(54) INSPECTION OF MICROELECTRONIC DEVICES USING NEAR-INFRARED LIGHT

(71) Applicant: Intel Corporation, Santa Clara, CA (US)

(72) Inventors: Liang W. Zhang, Chandler, AZ (US); Zhihua Zou, Gilbert, AZ (US); Osborne A. Martin, III, Maricopa, AZ (US); Robert F. Wiedmaier, Phoenix, AZ (US)

(73) Assignee: Intel Corporation, Santa Clara, CA (US)

( * ) Notice: Subject to any disclaimer, the term of this patent is extended or adjusted under 35 U.S.C. 154(b) by 80 days.

(21) Appl. No.: 15/245,442

(22) Filed: Aug. 24, 2016

(65) Prior Publication Data

US 2016/0363542 A1 Dec. 15, 2016

Related U.S. Application Data

(62) Division of application No. 14/229,824, filed on Mar. 28, 2014, now Pat. No. 9,488,595.

(51) Int. Cl.

| | |
|---|---|
| *G01B 11/14* | (2006.01) |
| *G03F 9/00* | (2006.01) |
| *H05K 3/00* | (2006.01) |
| *H05K 1/02* | (2006.01) |
| *G03F 7/20* | (2006.01) |
| *G01B 11/27* | (2006.01) |

(Continued)

(52) U.S. Cl.
CPC ............ *G01B 11/14* (2013.01); *G01B 11/272* (2013.01); *G01N 21/8806* (2013.01); *G01N 21/9501* (2013.01); *G03F 7/70775* (2013.01); *G03F 9/7007* (2013.01); *G03F 9/7046* (2013.01); *G03F 9/7065* (2013.01); *H01L 22/12* (2013.01); *H05K 1/0269* (2013.01); *H05K 3/0008* (2013.01); *G01B 11/18* (2013.01); *G01L 1/241* (2013.01); *G01L 1/248* (2013.01)

(58) Field of Classification Search
CPC .. G03F 7/70775; G03F 9/7003; G03F 9/7007; G03F 9/7046; G03F 9/7049; G03F 9/7065; G01N 21/9501; G01N 21/359; G01N 21/8806; H01L 22/12; H05K 1/0269; H05K 3/0008; G11B 11/14; G11B 11/27; G11B 11/272
See application file for complete search history.

(56) References Cited

U.S. PATENT DOCUMENTS

| | | |
|---|---|---|
| 3,378,407 A | 4/1968 | Keys |
| 4,173,820 A | 11/1979 | Frosch et al. |

(Continued)

*Primary Examiner* — Gordon J Stock, Jr.
(74) *Attorney, Agent, or Firm* — Schwabe, Williamson & Wyatt, P.C.

(57) ABSTRACT

Inspection of microelectronic devices is described using near infrared light. In one example, a dielectric material layer on a substrate is illuminated with a near infrared light beam. The substrate has at least one contact land, the dielectric material layer overlies at least a portion of the contact land, and the substrate has at least one via defined in the dielectric material layer, the via exposing at least a portion of the contact land. Reflected near infrared light is reflected from the substrate at a camera. The position of the via is determined relative to the contact land from the reflected light beam using an image processing device.

17 Claims, 7 Drawing Sheets

(51) Int. Cl.
*G01N 21/88* (2006.01)
*H01L 21/66* (2006.01)
*G01N 21/95* (2006.01)
*G01B 11/16* (2006.01)
*G01L 1/24* (2006.01)

(56) References Cited

U.S. PATENT DOCUMENTS

| | | | |
|---|---|---|---|
| 4,694,698 A | 9/1987 | Miyajima | |
| 4,789,236 A | 12/1988 | Hodor et al. | |
| 4,838,987 A * | 6/1989 | Dobson | H01L 21/30612 |
| | | | 219/121.69 |
| 5,177,555 A | 1/1993 | Stratton et al. | |
| 5,185,042 A | 2/1993 | Ferguson | |
| 5,728,944 A | 3/1998 | Nadolink | |
| 5,998,226 A * | 12/1999 | Chan | H01L 22/34 |
| | | | 257/E21.53 |
| 6,190,928 B1 * | 2/2001 | Lo | G03F 7/70633 |
| | | | 257/E21.53 |
| 6,253,623 B1 | 7/2001 | Joyce et al. | |
| 6,281,028 B1 * | 8/2001 | Bruce | H01L 23/544 |
| | | | 257/E23.179 |
| 7,038,224 B2 * | 5/2006 | Kadyshevitch | G01N 23/00 |
| | | | 250/492.1 |
| 7,945,087 B2 * | 5/2011 | Kotler | G05B 19/182 |
| | | | 250/491.1 |
| 8,399,264 B2 | 3/2013 | Zou et al. | |
| 8,431,421 B2 * | 4/2013 | Chen | H01L 22/34 |
| | | | 257/698 |
| 9,269,639 B2 * | 2/2016 | Fan | H01L 22/30 |
| 9,664,625 B2 * | 5/2017 | Zhou | G01N 21/9501 |
| 2009/0065772 A1 * | 3/2009 | Park | H01L 22/34 |
| | | | 257/48 |
| 2011/0043787 A1 | 2/2011 | Duran | |
| 2012/0287263 A1 * | 11/2012 | Zhou | G01N 21/9501 |
| | | | 348/126 |
| 2013/0247977 A1 | 9/2013 | Kumai et al. | |
| 2014/0022541 A1 | 1/2014 | Shapirov | |

* cited by examiner

INSPECTION OF MICROELECTRONIC DEVICES USING NEAR-INFRARED LIGHT

CROSS-REFERENCE TO RELATED APPLICATION

The present application is a division of prior U.S. patent application Ser. No. 14/229,824, filed Mar. 28, 2014, entitled "INSPECTION OF MICROELECTRONIC DEVICES USING NEAR-INFRARED LIGHT," by Liang W. Zhang, et al., the priority of which is hereby claimed and the contents of which are hereby incorporated by reference herein.

FIELD

The present description relates to microelectronic substrate fabrication and, in particular, to test and inspection using near infrared light (NIR).

BACKGROUND

As the size of microelectronic devices continues to decrease, the space or pitch between external attachment structures, such as solder bumps, for the microelectronic devices becomes smaller. As a result, the tolerances for the processes become smaller. These processes may include photolithography, used in forming the external attachment structures and their related structures within the microelectronic device. The processes may also include the formation of dielectric layers and the application of metal conductive traces. The external mounting elements, such as motherboard connection pads also become smaller and smaller and must be applied more precisely. These smaller tolerances increase the potential of misalignment, which may result in reliability issues and yield loss for the microelectronic devices.

In photolithography the alignment between different layers of a package substrate must have increasing precision for package substrate manufacturing. Layers such as solder resist layers must be aligned to Cu layers, and ABF layers to Cu layers.

Similarly with such package substrate connections, the quality of the solder joint affects the reliability of the package. Current tests for solder joint reliability are imprecise or require that the device being tested be destroyed.

BRIEF DESCRIPTION OF THE DRAWINGS

Embodiments of the invention are illustrated by way of example, and not by way of limitation, in the figures of the accompanying drawings in which like reference numerals refer to similar elements.

DETAILED DESCRIPTION

Figure 1:
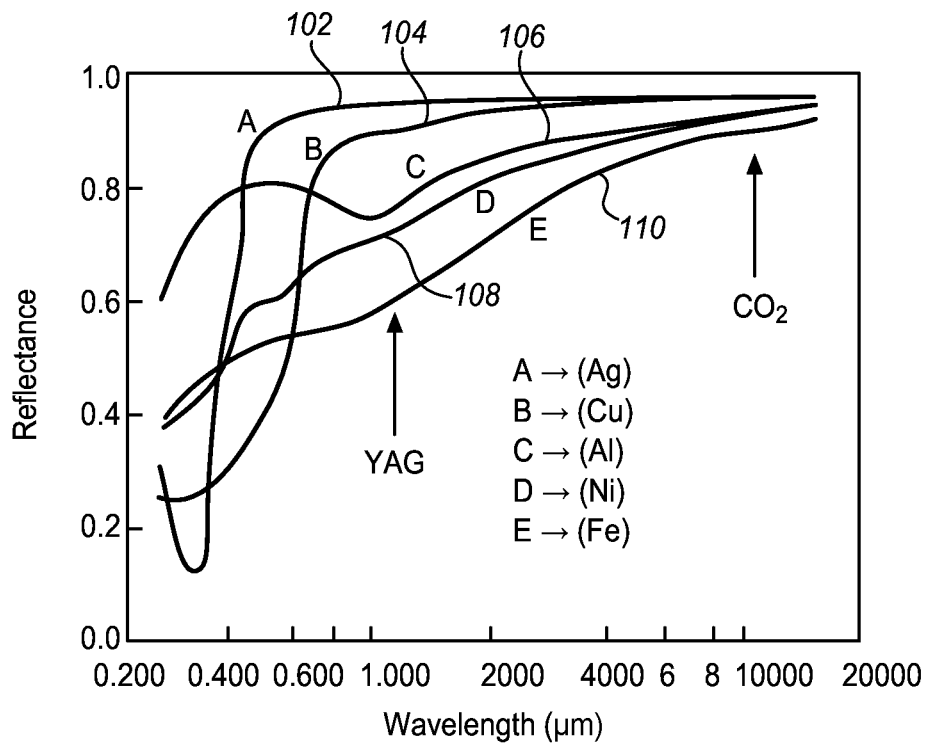
FIG. 1 is a diagram of reflectance for various materials at different IR wavelengths.
Figure 2:
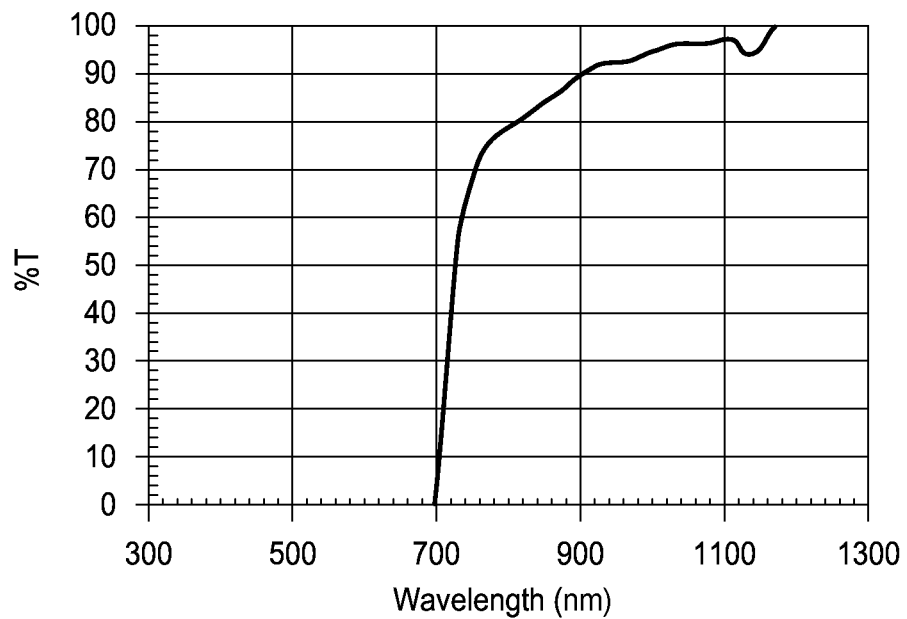
FIG. 2 is a diagram of the transmittance of solder resist at different wavelengths.

NIR (Near-Infrared Light) may be used to detect the edge of a Cu pad underneath a solder resist surface. NIR has a very strong reflectance from a Cu surface and very high transmission in a solder resist material. FIG. 1 is a graph of the reflectance of various metals on the vertical axis versus light wavelength on the horizontal axis. There is a curve for silver 102, copper 104, aluminum 106, nickel 108 and iron 110. As shown, silver and copper have a high reflectance from 500 nm and beyond past 8000 nm. All of the metals have reflectance of at least 50% from 500 nm and beyond. FIG. 2 is a graph of the transmittance of solder resist on the vertical axis versus wavelength on the horizontal axis. As shown solder resist is at least 80% transparent at about 750 nm and the transmittance increases at wavelengths up to about 1150 nm. As a result, any NIR from 750 nm to 1150 nm will be reflected by a metal pad and transmitted by solder resist and similar materials.

As a result, the signal of reflected light from a Cu pad surface may be very clear. With fluorescence techniques, the solder resist doesn't have a clear and complete boundary when the solder resist opening is very small. The thickness variations of the solder resist cause variations in the fluorescence which obscure the edges of the copper and of the solder resist. With NIR, the Cu pad underneath the solder resist has a clear and complete boundary at very small solder resist openings.

Figure 3:
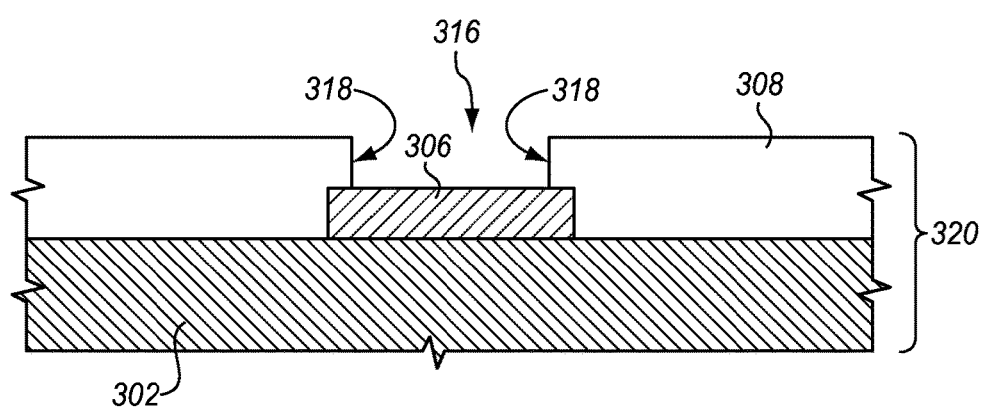
FIG. 3 is a side cross-sectional view of a contact land in a via on a portion of a substrate.

FIG. 3 is a side cross-sectional view of a portion of a package substrate 320. The package substrate has a support substrate 302 with a plurality of a contact lands 306 of which only one is shown. The contact land 306 may be any appropriate conductive material, including, but not limited to, copper, aluminum, silver, gold, and alloys thereof. The contact land 306 may be electrically connected to conductive traces (not shown) of the support substrate 302 through conductive vias and/or conductive traces (not shown). The package substrate 320 may be a portion of a printed circuit board or other similar circuit board used for mounting and forming communication between microelectronic devices. The package substrate may be a portion of an interposer used in conjunction with the fabrication of a microelectronic device package, or a portion of the microelectronic device itself. It may be a part of a socket, or a part of a motherboard or logic board.

The support substrate 302 may include a core (not shown) (e.g. bismaleimide triazine resin, FR4, polyimide materials, and the like) and a plurality of dielectric layers (not shown) (e.g. epoxy resin, polyimide, bisbenzocyclobutene, and the like) with conductive traces (not shown) (e.g. copper, aluminum, silver, gold, and the like) formed on each dielectric layer with conductive vias (not shown) (e.g. copper, aluminum, silver, gold, and the like) extending through each dielectric layer to connect the conductive traces, conductive lands, and/or electrical components, on different layers.

A dielectric layer 308 is deposited over the contact land 306 and the support substrate 302. The dielectric layers 308 are generally substantially opaque to visible light so that the contact land 306 cannot be seen clearly by the human eye under the dielectric layer 308. In one embodiment, the dielectric layer 308 may be one of the plurality of dielectric layers used in fabricating the supporting substrate. The first dielectric layer may comprise silica-filled epoxy, such as build-up films.

In another embodiment, the dielectric layer 308 may be a solder resist material, such as a polymer material. The solder resist material is used to ensure that a subsequently formed solder bump (not shown) remains in a desired area. The solder bump (not shown) may be used to connect the assembly to external devices (not shown).

At least one via 316, having at least one edge 318, may be formed in the dielectric layer 308. The via allows a solder ball or other structure to make and electrical connection to the contact pad. This allows an external connection into the wiring traces or paths inside the package substrate. In one embodiment, the via 316 may be formed using a lithographic process, in which an opening is patterned with a photoresist mask on the dielectric layer 308 and the via 316 is etched through the photoresist mask opening. The lithographic process may be used primarily in forming vias 316 in solder resist dielectric material layers 308. In another embodiment, the via 316 may be formed by laser drilling or ion drilling.

Figure 4:
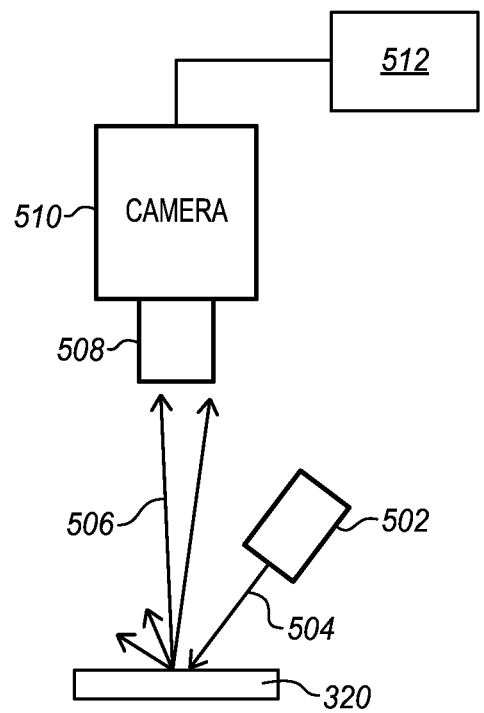
FIG. 4 is a diagram of an alignment inspection system according to an embodiment.

FIG. 4 is a diagram of an alignment inspection system 500 using near infrared light. The system includes a NIR light source 502 to direct a NIR light beam 504 onto the package substrate 320. The NIR propagates through the solder resist or other dielectric layers of the substrate and is reflected as a reflected beam 506 away from the substrate. Some of the reflected light 506 is incident on a NIR lens 508 and propagates through the lens to a NIR camera 510. The lens images the reflected light and may include an NIR filter to exclude other light. The filter may be a narrow band pass filter to block light other than that produced by the NIR light source. The camera image is sent to a processor 512 which includes processing resources and software to detect the contact pad edge. The results from the processor may be used to align the substrate 320 for photolithography.

The light source 502 may be any appropriate device, including a full-spectrum light generation device or a heater. In such a case a second NIR filter (not shown) may be used to limit the light to that of the desired wavelengths. The light receiving device 510 may be any appropriate light receiving device, such as a CCD (charge-coupled device) or CMOS (Complementary Metal Oxide Semiconductor) sensor-based camera.

In one embodiment, the light source 502 may generate the wide spectrum of infrared and visible light as a beam 504. The wide spectrum first light beam 504 may be passed through the light filter (not shown) to restrict the light to about 750 nm to 1150 nm or a narrow range within that range, such as about 1000 nm.

The incident light beam 504 is directed to the substrate and reflects from metal layers through the dielectric layer 308. As a result, the metal layers generate a return, but the dielectric layers do not. This allows the metal layers to be clearly observed. The reflected light 506 and any other ambient light is filtered and imaged by lens 508. The filter removes an incidental reflected light that is not in the appropriate NIR wavelengths such as wavelengths between about 750 nm to 1150 nm. The reflected light beam essentially transmits an image of the metal pads and other layers within the substrate.

Figure 5:
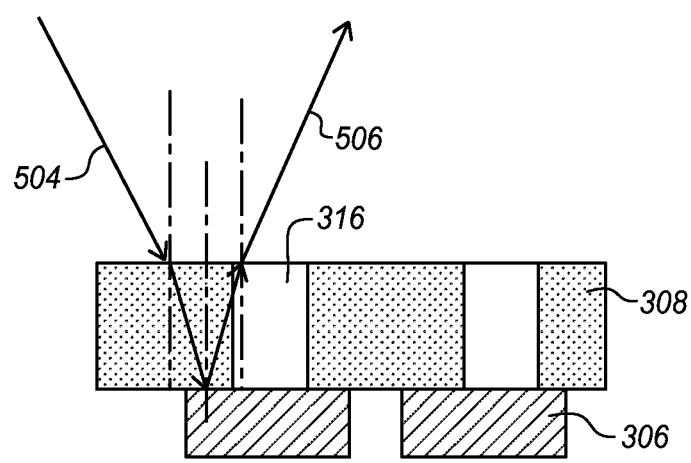
FIG. 5 is a diagram of a reflected light path for IR detection according to an embodiment.

FIG. 5 is a diagram of the reflection of the light path of FIG. 5 in more detail. The incident beam 504 of NIR transmits through the solder resist 308 and strikes the copper pads 306. It is then reflected back through the solder resist as reflected light 506 toward the camera 510. Other incident light 516 of a variety of different wavelengths may be absorbed or reflected, depending on the particular environment and the wavelengths. This other light may create a background noise level at the camera. The background noise may be reduced by filtering out unwanted light, i.e. light that is not being used in a measurement or in alignment detection.

Figure 6:
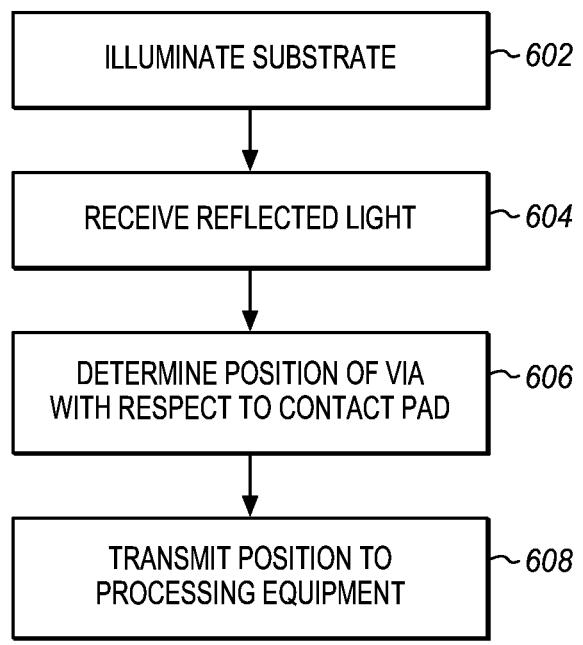
FIG. 6 is a process flow diagram of inspecting alignment according to an embodiment.

FIG. 6 is a process flow diagram of inspecting the alignment of an opening in a substrate as described herein. At 602 a NIR source light illuminates a substrate. The substrate has at least one contact land, a dielectric material layer is over at least a portion of the contact land, and a via is defined in the dielectric material layer to expose at least a portion of the contact land. At 604 light reflected from the substrate is received at a camera. At 606 the position of the via relative to the contact land may be determined from the reflected NIR light. At 608 the position determination may be transmitted to substrate processing equipment. The processing equipment may adjust the position of a mask or other equipment to form. This may be a mask for forming additional layers on the same substrate or it may be a mask used for subsequently formed substrates.

The apparatus of FIGS. 4 and 5 may also be used to determine solder joint quality after a die has been attached to a substrate such as a package substrate as described above. Using the NIR laser and camera, solder joint quality may be evaluated using a near infrared photo-elastic imaging technique. Solder joint defects cause an abnormal stress distribution as compared to good solder joints. The stress distribution can be measured by a near-infrared photo-elastic technique and this distribution can be used to indicate defects.

Figure 7:
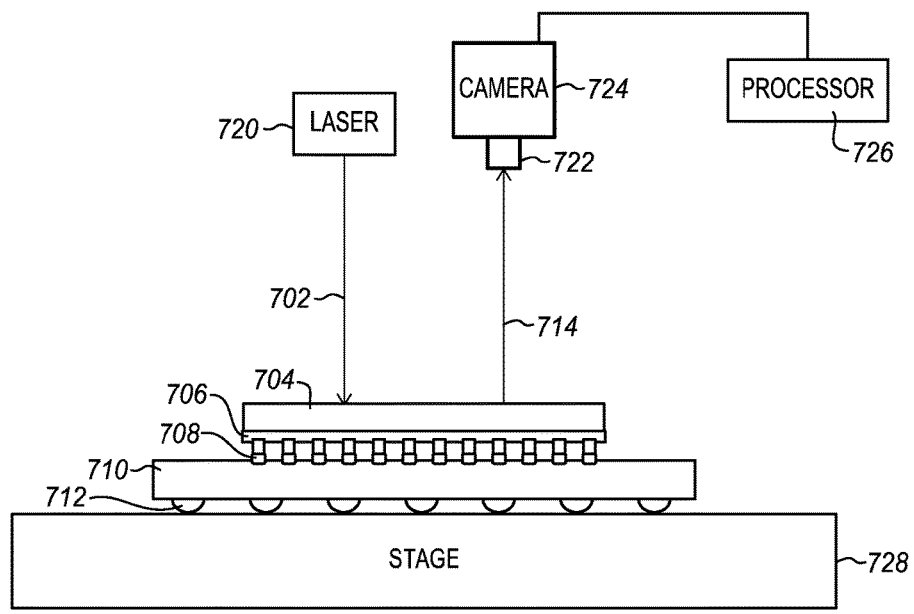
FIG. 7 is a diagram of solder joint inspection of a package using IR according to an embodiment.

FIG. 7 is a cross-sectional diagram of a microelectronic device 704, such as a silicon die with metal redistribution layers 706 soldered to a package substrate 710. The solder connection 708 between the die and the substrate may be any of a variety of different types, such as C4 (Controlled Collapse Chip Connection), solder bump, ball grid array, land grid array or any other type of solder connection. The package substrate has a second solder connection array 712 on the side opposite the microelectronic device, such as a ball grid array, land grid array or other connection. This second connection may be used to attach the package substrate to a PCB, such as a motherboard or logic board.

To measure the stress, a NIR light beam 702 from an appropriate source 720, such as a NIR laser is directed to the top of the microelectronic device 704. Silicon is transparent to NIR as are many of the structures in a silicon semiconductor device. The beam propagates through the silicon to the metal redistribution and solder layers below the silicon. The beam is then reflected from the metal and solder layers as a reflected beam 714. This beam is band pass filtered and imaged by appropriate optics 722 and received in a camera 724. The image data is sent to a processor 726 and analyzed to generate a stress map of the device. In order to scan the entire connection area of the solder joints, the device may be placed on a moving scanning stage 728. The stage moves the device laterally in two directions as the laser illuminates the device so that a larger area of the device can be illuminated by a narrow beam light source. Alternatively, the light source and camera may be moved or an optical system such as movable mirrors may be used to scan the illumination across the laser.

The stress method is much more robust than a 3-D X-ray or sawing method. A damaged bump connection on a silicon device has abnormal stress compared to neighboring good bumps. Such a stress evaluation may be used to test finished products prior to shipment and to evaluate product design and production processes to determine the quality of solder connections. Since the device is not harmed and does not need to be powered on during the test, such a test may be used to evaluate quality for products that are shipped to end users. If there are solder connection flaws, the package may be disassembled, cleaned and soldered again until the solder connections are good. This allows products that otherwise would be discarded to be repaired eliminating waste of the silicon die and reducing cost.

Figure 8:
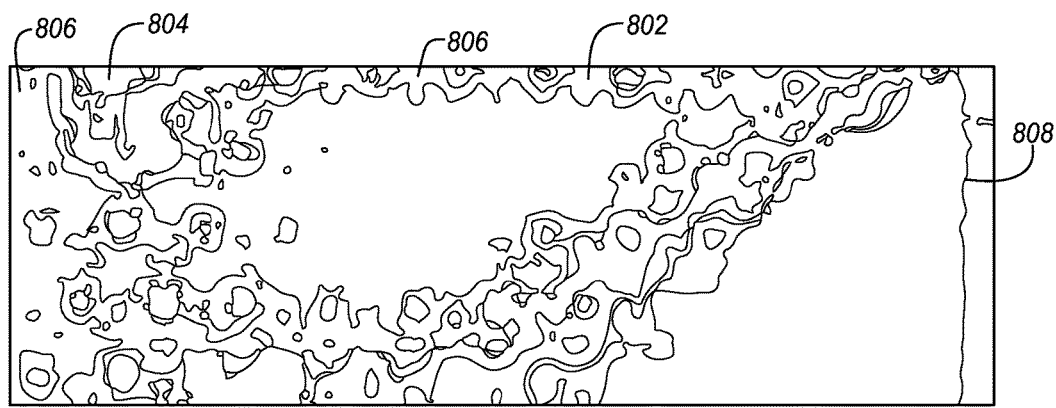
FIG. 8 is a diagram of a stress map according to an embodiment.

Using photo-elastic stress analysis, a stress map may be formed. The stress map may be used to identify failed solder joints. FIG. 8 is a diagram of an actual stress map from a soldered die and package rendered as contour lines to show the different values for the variations in stress. Such a diagram may be rendered using colors or any other presentation technique, depending on the particular implementation. This stress map is rendered as a top view of the imaged metal and solder layers. The low stress regions represent good solder connections and areas where there are no solder connections near the center of the device.

There is a high stress area 804 along the top left of the diagram indicating a poor or failed solder joint connection. This is surrounded by medium stress good connections 806. The top edge of the diagram corresponds to a row of solder joints in which a joint 804 at the end of the row is bad. There are several poor joints near the bad joint. The rest of the joints along the top edge of the diagram are good. At the right hand side of the top edge of the diagram, the die and the solder joints end. This is a high stress area 808 because the metal layers are unsupported by any solder connection. The bad solder joints may be identified by the amount of stress. High stress corresponds to a poor joint.

The photo-elastic stress solder joint evaluation system may be constructed using a number of elements. First a near infrared laser is used to illuminate the package. The laser is selected to have a wavelength that will be transmitted by the die such as a wavelength higher than about 1300 nm. The laser illuminates the die and a motorized stage may be used to move the sample package. This allows the entire connection area of the package to be scanned. The reflected light is then captured in a NIR camera or sensor. The results are then sent to a processor and analyzed using software to measure the stress using a photo-elastic method.

Figure 9:
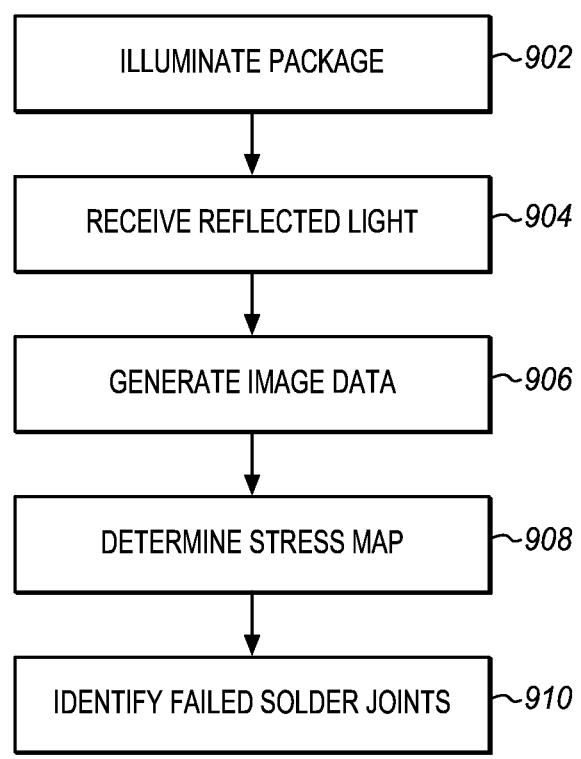
FIG. 9 is a process flow diagram of evaluating solder joints according to an embodiment.

FIG. 9 is a process flow diagram of testing or evaluating solder joint connections using a NIR imaging system. At 902 the package is illuminated using the NIR laser. The package is illuminated from the top of the die opposite the package substrate. The laser may be scanned over the entire top surface of the package. At 904 light that is reflected from the metal parts of the package is received at the imaging optics of the camera system. Since the silicon is transparent and the metal is reflective, the laser will be reflected from the metal redistribution and connection areas and from the solder.

At 906, the reflections received by the camera sensor are used to generate image data. At 908 this image data is sent to a processor to determine a stress map. At 910 the failed solder joints may be identified by the high stress areas. This identification may be done by the processor. If the processor has a map of the connection areas and can relate the connection areas to the image map, then the processor can determine whether there are any high stress areas within the solder connection area. This may be used as a simple pass/fail test or, with a more accurate map, the processor can identify specific failed connections.

The subject matter of the present description is not necessarily limited to the specific applications illustrated herein. The subject matter may be applied to other microelectronic device fabrication applications, including, but not limited to alignment inspection during the formation of trace routing layers (e.g. conductive via and trace formation on dielectric layers), during the fabrication of build-up layers on a microelectronic die, or during the formation of various components in a substrate. Furthermore, the subject matter may also be used in any appropriate application outside of the microelectronic device fabrication field.

Figure 10:
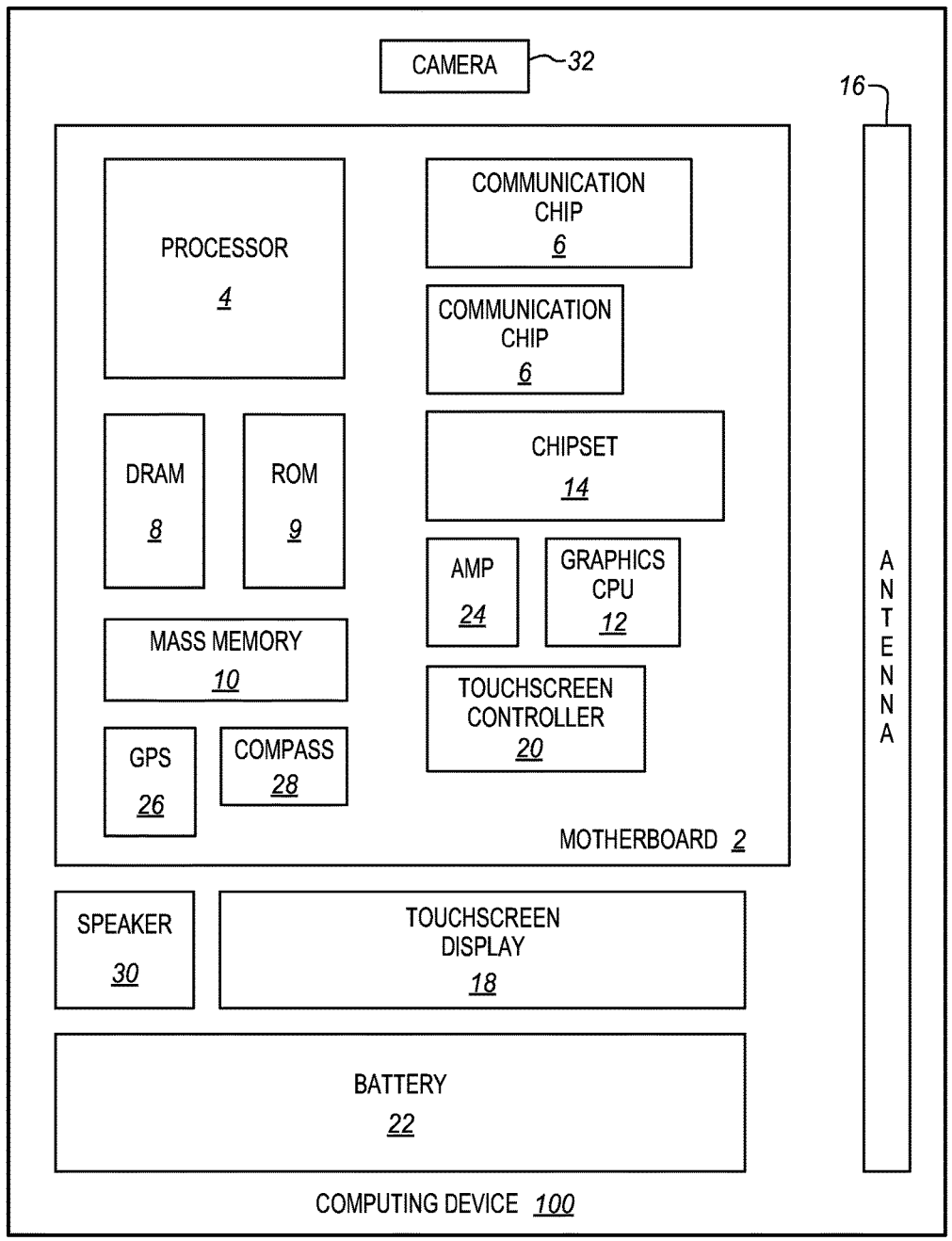
FIG. 10 is a block diagram of a computing device incorporating a tested semiconductor die according to an embodiment.

FIG. 10 illustrates a computing device 100 in accordance with one implementation of the invention. The computing device 100 houses a board 2. The board 2 may include a number of components, including but not limited to a processor 4 and at least one communication chip 6. The processor 4 is physically and electrically coupled to the board 2. In some implementations, the at least one communication chip 6 is also physically and electrically coupled to the board 2. In further implementations, the communication chip 6 is part of the processor 4.

Depending on its applications, computing device 100 may include other components that may or may not be physically and electrically coupled to the board 2. These other components include, but are not limited to, volatile memory (e.g., DRAM) 8, non-volatile memory (e.g., ROM) 9, flash memory (not shown), a graphics processor 12, a digital signal processor (not shown), a crypto processor (not shown), a chipset 14, an antenna 16, a display 18 such as a touchscreen display, a touchscreen controller 20, a battery 22, an audio codec (not shown), a video codec (not shown), a power amplifier 24, a global positioning system (GPS) device 26, a compass 28, an accelerometer (not shown), a gyroscope (not shown), a speaker 30, a camera 32, and a mass storage device (such as hard disk drive) 10, compact disk (CD) (not shown), digital versatile disk (DVD) (not shown), and so forth). These components may be connected to the system board 2, mounted to the system board, or combined with any of the other components.

The communication chip 6 enables wireless and/or wired communications for the transfer of data to and from the computing device 100. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 6 may implement any of a number of wireless or wired standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing device 100 may include a plurality of communication chips 6. For instance, a first communication chip 6 may be dedicated to shorter range wireless communications such as Wi-Fi and Bluetooth and a second communication chip 6 may be dedicated to longer range wireless communications such as GPS, EDGE, GPRS, CDMA, WiMAX, LTE, Ev-DO, and others.

The processor 4 of the computing device 100 includes an integrated circuit die packaged within the processor 4. In some implementations of the invention, the integrated circuit die of the processor, memory devices, communication devices, or other components include one or more dies that are inspected using NIR imaging, if desired. The term "processor" may refer to any device or portion of a device that processes electronic data from registers and/or memory to transform that electronic data into other electronic data that may be stored in registers and/or memory.

In various implementations, the computing device 100 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, the computing device 100 may be any other electronic device that processes data.

Embodiments may be implemented as a part of one or more memory chips, controllers, CPUs (Central Processing Unit), microchips or integrated circuits interconnected using a motherboard, an application specific integrated circuit (ASIC), and/or a field programmable gate array (FPGA).

References to "one embodiment", "an embodiment", "example embodiment", "various embodiments", etc., indicate that the embodiment(s) of the invention so described may include particular features, structures, or characteristics, but not every embodiment necessarily includes the particular features, structures, or characteristics. Further, some embodiments may have some, all, or none of the features described for other embodiments.

In the following description and claims, the term "coupled" along with its derivatives, may be used. "Coupled" is used to indicate that two or more elements co-operate or interact with each other, but they may or may not have intervening physical or electrical components between them.

As used in the claims, unless otherwise specified, the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

The following examples pertain to further embodiments. The various features of the different embodiments may be variously combined with some features included and others excluded to suit a variety of different applications. Some embodiments pertain to method for alignment detection that includes illuminating a dielectric material layer on a substrate with a near infrared light beam, wherein the substrate has at least one contact land, the dielectric material layer overlying at least a portion of the contact land, the substrate having at least one via defined in the dielectric material layer, the via exposing at least a portion of the contact land, receiving a reflected near infrared light beam from the substrate at a camera, and determining the position of the via relative to the contact land from the reflected light beam using an image processing device.

Further embodiments include accepting or rejecting the substrate based on the position of the via relative to the contact land.

Further embodiments include transmitting information from determining the position of the via relative to the contact land to substrate processing equipment.

Further embodiments include adjusting the substrate processing equipment to alter the position of via formation in subsequently formed substrates.

In further embodiments the illuminating the dielectric material layer comprises directing a first light beam having light wavelengths between about 700 nm and 1150 nm to the dielectric material layer.

Further embodiments include determining alignment as the distance between a center of the via and a center of the contact land.

In further embodiments the substrate comprises a package substrate having alternating dielectric and metal path way layers.

Further embodiments include adjusting a position of a photolithography mask based on the determined position.

Some embodiments pertain to a silicon connection alignment detector that includes a near infrared light beam source to illuminate a dielectric material layer on a substrate, wherein the substrate has at least one contact land, the dielectric material layer overlying at least a portion of the contact land, the substrate having at least one via defined in the dielectric material layer, the via exposing at least a portion of the contact land, a camera to receive a reflected near infrared light beam from the substrate, and an image processing device to determine the position of the via relative to the contact land from the reflected light beam.

Further embodiments include substrate processing equipment to receive the determined position of the via relative to the contact land to adjust the substrate processing equipment to alter the position of via formation in subsequently formed substrates.

In further embodiments the image processing device sends the determined position to substrate processing equipment for adjusting a position of a photolithography mask based on the determined position.

In further embodiments the image processing device determines alignment as the distance between a center of the via and a center of the contact land.

Some embodiments pertain to a method of solder joint quality detection that includes illuminating metal layers of a silicon device and a solder joint connection between the silicon device and a substrate by directing a near infrared light beam on to the silicon device, wherein the silicon device has a plurality of metal layers connected to solder joint connections and the substrate has a plurality of solder joint connections to the silicon device, receiving a reflected near infrared light beam from the metal layers and the solder joint connections at a camera, generating an image of the metal layers and the solder joint connections, analyzing photo-elastic stress of the metal and the solder joint connections in an image processing device using the generated image, and identifying failed solder joints using the stress map.

Further embodiments include moving the substrate during illuminating to scan the light beam over an area of the silicon device.

In further embodiments the near infrared light beam is selected so that the silicon device is substantially transparent to the near infrared light beam.

In further embodiments the near infrared light beam has a wavelength of 1300 nm or longer.

In further embodiments directing the light beam comprises directing the light beam on the top of the silicon device on a side opposite the substrate.

Some embodiments pertain to a solder joint quality detector that includes a near infrared light beam source to illuminate metal layers of a silicon device and a solder joint connection between the silicon device and a substrate, wherein the silicon device has a plurality of metal layers connected to solder joint connections and the substrate has a plurality of solder joint connections to the silicon device, a camera to receive a reflected near infrared light beam from the metal layers and the solder joint connections and to generate an image of the metal layers and the solder joint connections, and an image processing device to analyze photo-elastic stress of the metal and the solder joint connections using the generated image and to identify failed solder joints using the stress map.

In further embodiments the near infrared light beam source illuminates the silicon device with light that has a wavelength of 1300 nm or longer.

In further embodiments the near infrared light beam source directs the light beam on the top of the silicon device on a side opposite the substrate.

The invention claimed is:

1. A method comprising:
illuminating a dielectric material layer on a substrate with a near infrared light beam, wherein the substrate has at least one contact land, the dielectric material layer overlying at least a portion of the contact land, the substrate having at least one via defined in the dielectric material layer, the via exposing at least a portion of the contact land;
receiving a reflected near infrared light beam from the substrate at a camera; and
determining the position of the via relative to the contact land from the reflected near infrared light beam using an image processing device.

2. The method of claim 1, further comprising accepting or rejecting the substrate based on the position of the via relative to the contact land.

3. The method of claim 1, wherein the illuminating the dielectric material layer comprises directing a first light beam having light wavelengths between about 700 nm and 1150 nm to the dielectric material layer.

4. The method of claim 1, further comprising determining alignment as the distance between a center of the via and a center of the contact land.

5. The method of claim 1, wherein the substrate comprises a package substrate having alternating dielectric and metal path way layers.

6. The method of claim 1, further comprising adjusting a position of a photolithography mask based on the determined position.

7. The method of claim 1, further comprising moving the substrate during illuminating to scan the near infrared light beam over an area of a silicon device.

8. The method of claim 1, wherein the near infrared light beam is selected so that a silicon device is substantially transparent to the near infrared light beam.

9. The method of claim 1, wherein the near infrared light beam has a wavelength of 1300 nm or longer.

10. The method of claim 1, wherein a silicon device has a top on a side opposite the substrate and wherein directing the near infrared light beam comprises directing the near infrared light beam on the top of the silicon device.

11. The method of claim 1, further comprising transmitting information from determining the position of the via relative to the contact land.

12. The method of claim 11, further comprising altering a position of via formation in subsequently formed substrates.

13. An apparatus comprising:
a near infrared light beam source to illuminate a dielectric material layer on a substrate, wherein the substrate has at least one contact land, the dielectric material layer overlying at least a portion of the contact land, the substrate having at least one via defined in the dielectric material layer, the via exposing at least a portion of the contact land;
a camera to receive a reflected near infrared light beam from the substrate; and
an image processing device to determine the position of the via relative to the contact land from the reflected near infrared light beam.

14. The apparatus of claim 13, wherein the image processing device determines alignment as the distance between a center of the via and a center of the contact land.

15. The apparatus of claim 13, further comprising a scanner to move the substrate during illuminating to scan the near infrared light beam over an area of a silicon device.

16. The apparatus of claim 13, wherein the near infrared light beam source illuminates a silicon device with light that has a wavelength of 1300 nm or longer.

17. The apparatus of claim 13, wherein a silicon device has a top on a side opposite the substrate and wherein the near infrared light beam source directs the near infrared light beam on the top of the silicon device.

* * * * *